(12) United States Patent
Malkowski

(10) Patent No.: US 10,874,386 B2
(45) Date of Patent: Dec. 29, 2020

(54) SPECIMEN RETRIEVAL DEVICE

(71) Applicant: Covidien LP, Mansfield, MA (US)

(72) Inventor: Jaroslaw T. Malkowski, Trumbull, CT (US)

(73) Assignee: COVIDIEN LP, Mansfield, MA (US)

( * ) Notice: Subject to any disclaimer, the term of this patent is extended or adjusted under 35 U.S.C. 154(b) by 0 days.

(21) Appl. No.: 16/158,389

(22) Filed: Oct. 12, 2018

(65) Prior Publication Data
US 2019/0223855 A1    Jul. 25, 2019

Related U.S. Application Data

(60) Provisional application No. 62/621,189, filed on Jan. 24, 2018.

(51) Int. Cl.
| | | |
|---|---|---|
| *A61B 17/02* | (2006.01) | |
| *A61M 1/00* | (2006.01) | |
| *A61M 39/24* | (2006.01) | |
| *A61B 17/34* | (2006.01) | |
| *A61B 17/00* | (2006.01) | |

(Continued)

(52) U.S. Cl.
CPC .... *A61B 17/0218* (2013.01); *A61B 17/00234* (2013.01); *A61B 17/0293* (2013.01); *A61B 17/3423* (2013.01); *A61M 1/0035* (2014.02); *A61M 1/0068* (2014.02); *A61M 39/24* (2013.01); *A61B 10/02* (2013.01); *A61B 2017/00287* (2013.01); *A61B 2017/00526* (2013.01); *A61B 2017/00862* (2013.01); *A61B 2017/0225* (2013.01);

(Continued)

(58) Field of Classification Search
CPC ................. A61B 17/3421–3431; A61B 17/34
See application file for complete search history.

(56) References Cited

U.S. PATENT DOCUMENTS

| | | |
|---|---|---|
| 30,471 A | 10/1860 | Dudley |
| 35,164 A | 5/1862 | Logan et al. |

(Continued)

FOREIGN PATENT DOCUMENTS

| | | |
|---|---|---|
| DE | 3542667 A1 | 6/1986 |
| DE | 8435489 U1 | 8/1986 |

(Continued)

OTHER PUBLICATIONS

European Search Report EP 12191639.9 dated Feb. 20, 2013.

(Continued)

*Primary Examiner* — Eduardo C Robert
*Assistant Examiner* — Michelle C Eckman

(57) ABSTRACT

A surgical apparatus of the present disclosure includes a wound retractor having a specimen bag attached thereto. Kits of the present disclosure include the surgical apparatus and a vacuum tube. In embodiments, the vacuum tube may be introduced into a lumen of the wound retractor. A vacuum source is attached to a proximal end portion of the vacuum tube to draw a vacuum through the vacuum tube, which in turn draws a tissue specimen into the lumen of the vacuum tube through an opening in the distal end portion of the vacuum tube. The vacuum tube, possessing the tissue specimen therein, may then be removed from the wound retractor. Methods for using the surgical apparatus and/or kits of the present disclosure are also provided.

17 Claims, 10 Drawing Sheets

(51) Int. Cl.
    *A61B 17/30*         (2006.01)
    *A61B 10/02*         (2006.01)

(52) U.S. Cl.
    CPC . *A61B 2017/306* (2013.01); *A61B 2017/3429* (2013.01); *A61B 2217/005* (2013.01); *A61M 2039/248* (2013.01)

(56) References Cited

U.S. PATENT DOCUMENTS

| | | |
|---|---|---|
| 156,477 A | 11/1874 | Bradford |
| 1,609,014 A | 11/1926 | Dowd |
| 3,800,781 A | 4/1974 | Zalucki |
| 4,557,255 A | 12/1985 | Goodman |
| 4,611,594 A | 9/1986 | Grayhack et al. |
| 4,744,363 A | 5/1988 | Hasson |
| 4,790,812 A | 12/1988 | Hawkins, Jr. et al. |
| 4,852,586 A | 8/1989 | Haines |
| 4,927,427 A | 5/1990 | Kriauciunas et al. |
| 4,977,903 A | 12/1990 | Haines |
| 4,991,593 A | 2/1991 | LeVahn |
| 4,997,435 A | 3/1991 | Demeter |
| 5,037,379 A | 8/1991 | Clayman et al. |
| 5,074,867 A | 12/1991 | Wilk |
| 5,084,054 A | 1/1992 | Bencini et al. |
| 5,143,082 A | 9/1992 | Kindberg et al. |
| 5,147,371 A | 9/1992 | Washington et al. |
| 5,176,687 A | 1/1993 | Hasson et al. |
| 5,190,542 A | 3/1993 | Nakao et al. |
| 5,190,555 A | 3/1993 | Wetter et al. |
| 5,190,561 A | 3/1993 | Graber |
| 5,192,284 A | 3/1993 | Pleatman |
| 5,192,286 A | 3/1993 | Phan et al. |
| 5,201,740 A | 4/1993 | Nakao et al. |
| 5,215,521 A | 6/1993 | Cochran et al. |
| 5,224,930 A | 7/1993 | Spaeth et al. |
| 5,234,439 A | 8/1993 | Wilk et al. |
| 5,279,539 A | 1/1994 | Bohan et al. |
| 5,312,416 A | 5/1994 | Spaeth et al. |
| 5,320,627 A | 6/1994 | Sorensen et al. |
| 5,330,483 A | 7/1994 | Heaven et al. |
| 5,336,227 A | 8/1994 | Nakao et al. |
| 5,337,754 A | 8/1994 | Heaven et al. |
| 5,341,815 A | 8/1994 | Cofone et al. |
| 5,352,184 A | 10/1994 | Goldberg et al. |
| 5,354,303 A | 10/1994 | Spaeth et al. |
| 5,368,545 A * | 11/1994 | Schaller ............ A61B 17/00234 128/846 |
| 5,368,597 A | 11/1994 | Pagedas |
| 5,370,647 A | 12/1994 | Graber et al. |
| 5,443,472 A | 8/1995 | Li |
| 5,465,731 A | 11/1995 | Bell et al. |
| 5,480,404 A | 1/1996 | Kammerer et al. |
| 5,486,182 A | 1/1996 | Nakao et al. |
| 5,486,183 A | 1/1996 | Middleman et al. |
| 5,499,988 A | 3/1996 | Espiner et al. |
| 5,524,633 A | 6/1996 | Heaven et al. |
| 5,524,644 A * | 6/1996 | Crook ................ A61B 17/0293 128/888 |
| 5,535,759 A | 7/1996 | Wilk |
| 5,611,803 A | 3/1997 | Heaven et al. |
| 5,618,296 A * | 4/1997 | Sorensen ......... A61B 17/32002 606/167 |
| 5,630,822 A | 5/1997 | Hermann et al. |
| 5,642,282 A | 6/1997 | Sonehara |
| 5,643,282 A | 7/1997 | Kieturakis |
| 5,643,283 A | 7/1997 | Younker |
| 5,645,083 A | 7/1997 | Essig et al. |
| 5,647,372 A | 7/1997 | Tovey et al. |
| 5,649,902 A | 7/1997 | Yoon |
| 5,658,296 A | 8/1997 | Bates et al. |
| 5,679,423 A | 10/1997 | Shah |
| 5,681,324 A | 10/1997 | Kammerer et al. |
| 5,720,754 A | 2/1998 | Middleman et al. |
| 5,735,289 A | 4/1998 | Pfeffer et al. |
| 5,741,271 A | 4/1998 | Nakao et al. |
| 5,755,724 A | 5/1998 | Yoon |
| 5,759,187 A | 6/1998 | Nakao et al. |
| 5,769,794 A | 6/1998 | Conlan et al. |
| 5,782,840 A | 7/1998 | Nakao |
| 5,785,677 A | 7/1998 | Auweiler |
| 5,788,709 A | 8/1998 | Riek et al. |
| 5,792,145 A | 8/1998 | Bates et al. |
| 5,814,044 A | 9/1998 | Hooven |
| 5,829,440 A | 11/1998 | Broad, Jr. |
| 5,836,953 A | 11/1998 | Yoon |
| 5,853,374 A * | 12/1998 | Hart ................ A61B 17/00234 600/562 |
| 5,895,392 A | 4/1999 | Riek et al. |
| 5,904,690 A | 5/1999 | Middleman et al. |
| 5,906,621 A | 5/1999 | Secrest et al. |
| 5,908,429 A | 6/1999 | Yoon |
| 5,957,884 A | 9/1999 | Hooven |
| 5,971,995 A | 10/1999 | Rousseau |
| 5,980,544 A | 11/1999 | Vaitekunas |
| 5,997,547 A | 12/1999 | Nakao et al. |
| 6,004,330 A | 12/1999 | Middleman et al. |
| 6,007,512 A | 12/1999 | Hooven |
| 6,007,546 A | 12/1999 | Snow et al. |
| 6,019,770 A | 2/2000 | Christoudias |
| 6,033,428 A * | 3/2000 | Sardella ............ A61B 17/3423 606/213 |
| 6,036,681 A | 3/2000 | Hooven |
| 6,059,793 A | 5/2000 | Pagedas |
| 6,123,701 A | 9/2000 | Nezhat |
| 6,152,932 A | 11/2000 | Ternstrom |
| 6,156,055 A | 12/2000 | Ravenscroft |
| 6,162,235 A | 12/2000 | Vaitekunas |
| 6,165,121 A | 12/2000 | Alferness |
| 6,168,603 B1 | 1/2001 | Leslie et al. |
| 6,206,889 B1 | 3/2001 | Bennardo |
| 6,228,095 B1 | 5/2001 | Dennis |
| 6,254,534 B1 * | 7/2001 | Butler ...................... A61B 1/32 600/206 |
| 6,258,102 B1 | 7/2001 | Pagedas |
| 6,264,663 B1 | 7/2001 | Cano |
| 6,270,505 B1 | 8/2001 | Yoshida et al. |
| 6,277,083 B1 | 8/2001 | Eggers et al. |
| 6,280,450 B1 | 8/2001 | McGuckin, Jr. |
| 6,344,026 B1 | 2/2002 | Burbank et al. |
| 6,348,056 B1 | 2/2002 | Bates et al. |
| 6,350,266 B1 | 2/2002 | White et al. |
| 6,350,267 B1 | 2/2002 | Stefanchik |
| 6,368,328 B1 | 4/2002 | Chu et al. |
| 6,383,195 B1 | 5/2002 | Richard |
| 6,383,196 B1 | 5/2002 | Leslie et al. |
| 6,383,197 B1 | 5/2002 | Conlon et al. |
| 6,387,102 B2 | 5/2002 | Pagedas |
| 6,406,440 B1 | 6/2002 | Stefanchik |
| 6,409,733 B1 | 6/2002 | Conlon et al. |
| 6,419,639 B2 | 7/2002 | Walther et al. |
| 6,447,523 B1 | 9/2002 | Middleman et al. |
| 6,471,659 B2 | 10/2002 | Eggers et al. |
| 6,506,166 B1 | 1/2003 | Hendler et al. |
| 6,508,773 B2 | 1/2003 | Burbank et al. |
| 6,537,273 B1 | 3/2003 | Sosiak et al. |
| 6,547,310 B2 | 4/2003 | Myers |
| 6,589,252 B2 | 7/2003 | McGuckin, Jr. |
| 6,752,811 B2 | 6/2004 | Chu et al. |
| 6,755,779 B2 | 6/2004 | Vanden Hoek et al. |
| 6,780,193 B2 | 8/2004 | Leslie et al. |
| 6,805,699 B2 | 10/2004 | Shimm |
| 6,840,948 B2 | 1/2005 | Albrecht et al. |
| 6,872,211 B2 | 3/2005 | White et al. |
| 6,887,255 B2 | 5/2005 | Shimm |
| 6,958,069 B2 | 10/2005 | Shipp et al. |
| 6,971,988 B2 | 12/2005 | Orban, III |
| 6,994,696 B2 | 2/2006 | Suga |
| 7,014,648 B2 | 3/2006 | Ambrisco et al. |
| 7,018,373 B2 | 3/2006 | Suzuki |
| 7,052,454 B2 * | 5/2006 | Taylor ................ A61B 17/3423 600/114 |
| 7,052,501 B2 | 5/2006 | McGuckin, Jr. |
| 7,090,637 B2 | 8/2006 | Danitz et al. |

(56) References Cited

U.S. PATENT DOCUMENTS

| | | | |
|---|---|---|---|
| 7,115,125 B2 | 10/2006 | Nakao et al. | |
| 7,270,663 B2 | 9/2007 | Nakao | |
| 7,273,488 B2 | 9/2007 | Nakamura et al. | |
| 7,410,491 B2 | 8/2008 | Hopkins et al. | |
| 7,537,564 B2* | 5/2009 | Bonadio | A61B 17/0293 600/208 |
| 7,547,310 B2 | 6/2009 | Whitfield | |
| 7,618,437 B2 | 11/2009 | Nakao | |
| 7,670,346 B2 | 3/2010 | Whitfield | |
| 7,722,626 B2 | 5/2010 | Middleman et al. | |
| 7,762,959 B2 | 7/2010 | Bilsbury | |
| 7,785,251 B2 | 8/2010 | Wilk | |
| 7,819,121 B2 | 10/2010 | Amer | |
| 7,837,612 B2 | 11/2010 | Gill et al. | |
| RE42,050 E | 1/2011 | Richard | |
| 7,892,242 B2 | 2/2011 | Goldstein | |
| 7,955,292 B2* | 6/2011 | Leroy | A61B 17/00234 206/216 |
| 7,998,068 B2* | 8/2011 | Bonadio | A61B 17/3423 600/208 |
| 8,016,771 B2 | 9/2011 | Orban, III | |
| 8,057,485 B2 | 11/2011 | Hollis et al. | |
| 8,075,567 B2 | 12/2011 | Taylor et al. | |
| 8,097,001 B2 | 1/2012 | Nakao | |
| 8,152,820 B2 | 4/2012 | Mohamed et al. | |
| 8,172,772 B2 | 5/2012 | Zwolinski et al. | |
| 8,206,401 B2 | 6/2012 | Nakao | |
| 8,251,900 B2* | 8/2012 | Ortiz | A61B 17/3423 600/208 |
| 8,337,510 B2 | 12/2012 | Rieber et al. | |
| 8,343,031 B2 | 1/2013 | Gertner | |
| 8,348,827 B2 | 1/2013 | Zwolinski | |
| 8,388,630 B2 | 3/2013 | Teague et al. | |
| 8,409,112 B2 | 4/2013 | Wynne et al. | |
| 8,409,216 B2 | 4/2013 | Parihar et al. | |
| 8,409,217 B2 | 4/2013 | Parihar et al. | |
| 8,414,596 B2 | 4/2013 | Parihar et al. | |
| 8,419,749 B2 | 4/2013 | Shelton, IV et al. | |
| 8,425,533 B2 | 4/2013 | Parihar et al. | |
| 8,430,826 B2 | 4/2013 | Uznanski et al. | |
| 8,435,237 B2 | 5/2013 | Bahney | |
| 8,444,655 B2 | 5/2013 | Parihar et al. | |
| 8,550,992 B2* | 10/2013 | Kleyman | A61B 17/3423 600/206 |
| 8,579,914 B2 | 11/2013 | Menn et al. | |
| 8,585,712 B2 | 11/2013 | O'Prey et al. | |
| 8,591,521 B2 | 11/2013 | Cherry et al. | |
| 8,652,147 B2* | 2/2014 | Hart | A61B 17/00234 606/114 |
| 8,696,683 B2 | 4/2014 | LeVert | |
| 8,721,658 B2 | 5/2014 | Kahle et al. | |
| 8,734,464 B2 | 5/2014 | Grover et al. | |
| 8,777,961 B2 | 7/2014 | Cabrera et al. | |
| 8,795,291 B2 | 8/2014 | Davis et al. | |
| 8,821,377 B2 | 9/2014 | Collins | |
| 8,827,968 B2 | 9/2014 | Taylor et al. | |
| 8,870,894 B2 | 10/2014 | Taylor et al. | |
| 8,906,035 B2 | 12/2014 | Zwolinski et al. | |
| 8,906,036 B2 | 12/2014 | Farascioni | |
| 8,956,370 B2 | 2/2015 | Taylor et al. | |
| 8,968,329 B2 | 3/2015 | Cabrera | |
| 9,017,249 B2* | 4/2015 | Smith | A61B 17/3423 600/204 |
| 9,033,873 B2* | 5/2015 | Kleyman | A61B 17/0293 600/208 |
| 9,078,696 B2* | 7/2015 | Kleyman | A61B 17/3431 |
| 9,084,594 B2* | 7/2015 | Suh | A61B 17/0218 |
| 9,707,011 B2* | 7/2017 | Malkowski | A61B 17/3494 |
| 9,717,522 B2* | 8/2017 | Albrecht | A61B 17/0218 |
| 9,867,604 B2* | 1/2018 | Hart | A61B 17/0293 |
| 9,901,329 B1* | 2/2018 | Polo | A61B 17/32002 |
| 9,986,986 B2* | 6/2018 | Radl | A61B 17/00234 |
| 10,045,877 B2* | 8/2018 | Weig | A61F 5/445 |
| 10,172,641 B2* | 1/2019 | Wachli | A61B 17/3423 |
| 10,405,877 B2* | 9/2019 | Radl | A61B 17/3205 |
| 10,420,578 B2* | 9/2019 | Racenet | A61B 17/320016 |
| 2002/0068943 A1 | 6/2002 | Chu et al. | |
| 2002/0082516 A1 | 6/2002 | Stefanchik | |
| 2003/0073970 A1 | 4/2003 | Suga | |
| 2003/0100909 A1 | 5/2003 | Suzuki | |
| 2003/0100919 A1 | 5/2003 | Hopkins et al. | |
| 2003/0199915 A1 | 10/2003 | Shimm | |
| 2003/0216773 A1 | 11/2003 | Shimm | |
| 2004/0049099 A1* | 3/2004 | Ewers | A61B 1/32 600/206 |
| 2004/0092796 A1* | 5/2004 | Butler | A61B 17/0293 600/208 |
| 2004/0097960 A1 | 5/2004 | Terachi et al. | |
| 2004/0138587 A1 | 7/2004 | Lyons | |
| 2004/0225192 A1* | 11/2004 | Young | A61B 17/34 600/204 |
| 2005/0085808 A1 | 4/2005 | Nakao | |
| 2005/0090717 A1* | 4/2005 | Bonadio | A61B 17/0293 600/208 |
| 2005/0165411 A1 | 7/2005 | Orban | |
| 2005/0256425 A1 | 11/2005 | Prusiner | |
| 2005/0267492 A1 | 12/2005 | Poncet et al. | |
| 2006/0025781 A1* | 2/2006 | Young | A61B 17/0218 606/114 |
| 2006/0030750 A1 | 2/2006 | Amer | |
| 2006/0052799 A1 | 3/2006 | Middleman et al. | |
| 2006/0058776 A1 | 3/2006 | Bilsbury | |
| 2006/0169287 A1 | 8/2006 | Harrison et al. | |
| 2006/0200169 A1 | 9/2006 | Sniffin | |
| 2006/0200170 A1 | 9/2006 | Aranyi | |
| 2006/0229639 A1 | 10/2006 | Whitfield | |
| 2006/0229640 A1 | 10/2006 | Whitfield | |
| 2007/0016224 A1 | 1/2007 | Nakao | |
| 2007/0016225 A1 | 1/2007 | Nakao | |
| 2007/0073251 A1 | 3/2007 | Zhou et al. | |
| 2007/0088370 A1 | 4/2007 | Kahle et al. | |
| 2007/0135780 A1 | 6/2007 | Pagedas | |
| 2007/0135781 A1 | 6/2007 | Hart | |
| 2007/0186935 A1 | 8/2007 | Wang et al. | |
| 2008/0188766 A1 | 8/2008 | Gertner | |
| 2008/0221587 A1 | 9/2008 | Schwartz | |
| 2008/0221588 A1 | 9/2008 | Hollis et al. | |
| 2008/0234696 A1 | 9/2008 | Taylor et al. | |
| 2008/0300621 A1 | 12/2008 | Hopkins et al. | |
| 2008/0312496 A1 | 12/2008 | Zwolinski | |
| 2009/0043315 A1* | 2/2009 | Moon | A61B 17/00234 606/114 |
| 2009/0082779 A1 | 3/2009 | Nakao | |
| 2009/0182292 A1 | 7/2009 | Egle et al. | |
| 2009/0192510 A1 | 7/2009 | Bahney | |
| 2009/0240238 A1 | 9/2009 | Grodrian et al. | |
| 2010/0000471 A1 | 1/2010 | Hibbard | |
| 2010/0152746 A1 | 6/2010 | Ceniccola et al. | |
| 2010/0219091 A1* | 9/2010 | Turner | A61B 17/00234 206/438 |
| 2010/0228091 A1* | 9/2010 | Widenhouse | A61B 17/3423 600/203 |
| 2010/0249516 A1* | 9/2010 | Shelton, IV | A61B 17/0293 600/203 |
| 2010/0256662 A1* | 10/2010 | Racenet | A61B 10/06 606/170 |
| 2010/0312063 A1* | 12/2010 | Hess | A61B 17/3423 600/204 |
| 2010/0312064 A1* | 12/2010 | Weisenburgh, II | A61B 17/0057 600/206 |
| 2011/0011410 A1* | 1/2011 | Desai | A61B 17/0293 128/898 |
| 2011/0054258 A1* | 3/2011 | O'Keefe | A61B 17/3423 600/206 |
| 2011/0066001 A1* | 3/2011 | Shelton, IV | A61B 17/0293 600/208 |
| 2011/0071359 A1* | 3/2011 | Bonadio | A61B 17/3423 600/184 |
| 2011/0071473 A1* | 3/2011 | Rogers | A61B 17/0218 604/167.01 |
| 2011/0087235 A1 | 4/2011 | Taylor et al. | |

(56) References Cited

U.S. PATENT DOCUMENTS

| | | | |
|---|---|---|---|
| 2011/0184311 A1 | 7/2011 | Parihar et al. | |
| 2011/0184434 A1 | 7/2011 | Parihar et al. | |
| 2011/0184435 A1 | 7/2011 | Parihar et al. | |
| 2011/0184436 A1 | 7/2011 | Shelton, IV et al. | |
| 2011/0190779 A1 | 8/2011 | Gell et al. | |
| 2011/0190781 A1 | 8/2011 | Collier et al. | |
| 2011/0190782 A1 | 8/2011 | Fleming et al. | |
| 2011/0213297 A1* | 9/2011 | Aklog | A61B 17/22 604/28 |
| 2011/0251464 A1* | 10/2011 | Kleyman | A61B 17/3423 600/206 |
| 2011/0264091 A1* | 10/2011 | Koppleman | A61B 17/00491 606/41 |
| 2011/0282237 A1* | 11/2011 | Conlon | A61B 17/3423 600/562 |
| 2011/0299799 A1 | 12/2011 | Towe | |
| 2012/0046667 A1 | 2/2012 | Cherry et al. | |
| 2012/0083795 A1 | 4/2012 | Fleming et al. | |
| 2012/0083796 A1 | 4/2012 | Grover et al. | |
| 2012/0089151 A1* | 4/2012 | Taylor | A61B 17/00234 606/114 |
| 2012/0095297 A1* | 4/2012 | Dang | A61B 17/0218 600/208 |
| 2012/0203241 A1 | 8/2012 | Williamson, IV | |
| 2013/0023895 A1 | 1/2013 | Saleh | |
| 2013/0103042 A1 | 4/2013 | Davis | |
| 2013/0116592 A1 | 5/2013 | Whitfield | |
| 2013/0172684 A1* | 7/2013 | Smith | A61B 17/3423 600/208 |
| 2013/0184536 A1* | 7/2013 | Shibley | A61B 17/00234 600/235 |
| 2013/0190773 A1 | 7/2013 | Carlson | |
| 2013/0218170 A1 | 8/2013 | Uznanski et al. | |
| 2013/0225932 A1* | 8/2013 | Smith | A61B 1/313 600/206 |
| 2013/0245381 A1* | 9/2013 | Dang | A61B 17/0218 600/208 |
| 2013/0245636 A1 | 9/2013 | Jansen | |
| 2013/0253267 A1* | 9/2013 | Collins | A61B 17/221 600/104 |
| 2013/0274758 A1 | 10/2013 | Young et al. | |
| 2013/0325025 A1 | 12/2013 | Hathaway et al. | |
| 2014/0046337 A1 | 2/2014 | O'Prey et al. | |
| 2014/0058403 A1* | 2/2014 | Menn | A61B 17/00234 606/114 |
| 2014/0180303 A1 | 6/2014 | Duncan et al. | |
| 2014/0222016 A1 | 8/2014 | Grover et al. | |
| 2014/0236110 A1 | 8/2014 | Taylor et al. | |
| 2014/0236168 A1* | 8/2014 | Shibley | A61B 17/0218 606/114 |
| 2014/0243865 A1 | 8/2014 | Swayze et al. | |
| 2014/0249541 A1 | 9/2014 | Kahle et al. | |
| 2014/0276913 A1 | 9/2014 | Tah et al. | |
| 2014/0303640 A1 | 10/2014 | Davis et al. | |
| 2014/0309656 A1 | 10/2014 | Gal et al. | |
| 2014/0330285 A1 | 11/2014 | Rosenblatt et al. | |
| 2014/0350567 A1 | 11/2014 | Schmitz et al. | |
| 2014/0371759 A1 | 12/2014 | Hartoumbekis | |
| 2014/0371760 A1 | 12/2014 | Menn | |
| 2015/0018837 A1 | 1/2015 | Sartor et al. | |
| 2015/0045808 A1 | 2/2015 | Farasconi | |
| 2015/0087913 A1* | 3/2015 | Dang | A61B 17/3423 600/204 |
| 2015/0230781 A1 | 8/2015 | Loktionov et al. | |
| 2015/0272556 A1* | 10/2015 | Lee | A61B 10/06 600/566 |
| 2015/0272620 A1* | 10/2015 | Zisow | A61B 17/3205 600/204 |
| 2015/0305772 A1* | 10/2015 | McCauley | A61B 17/3423 606/114 |
| 2016/0030073 A1* | 2/2016 | Isakov | A61B 17/32056 606/113 |
| 2016/0066899 A1* | 3/2016 | Lovell | A61B 17/3421 606/112 |
| 2016/0100857 A1* | 4/2016 | Wachli | A61B 17/3439 600/204 |
| 2016/0262794 A1* | 9/2016 | Wachli | A61B 17/3423 |
| 2016/0338682 A1* | 11/2016 | Hoyte | A61B 17/00234 |
| 2017/0049427 A1* | 2/2017 | Do | A61B 17/00234 |
| 2017/0056065 A1* | 3/2017 | Do | A61B 17/3423 |
| 2017/0181767 A1* | 6/2017 | Makey | A61B 17/3423 |
| 2017/0215862 A1* | 8/2017 | Pravongviengkham | A61B 17/3417 |
| 2017/0224321 A1* | 8/2017 | Kessler | A61B 17/00234 |
| 2017/0252026 A1* | 9/2017 | Gupta | A61B 17/00234 |
| 2017/0280988 A1* | 10/2017 | Barbato | A61B 1/00016 |
| 2017/0325657 A1* | 11/2017 | Prior | A61B 1/00 |
| 2017/0325798 A1* | 11/2017 | Prior | A61B 17/0218 |
| 2017/0325800 A1* | 11/2017 | Prior | A61B 17/0293 |
| 2018/0172168 A1* | 6/2018 | Waldron | F16K 15/202 |
| 2018/0199961 A1* | 7/2018 | Prior | A61B 17/3421 |
| 2018/0206866 A1* | 7/2018 | Wan | A61B 17/2202 |
| 2018/0338773 A1* | 11/2018 | Parys | A61B 17/32002 |
| 2019/0167291 A1* | 6/2019 | Prior | A61B 17/32002 |
| 2019/0209194 A1* | 7/2019 | Sartor | A61B 17/00234 |
| 2019/0223855 A1* | 7/2019 | Malkowski | A61B 17/00234 |
| 2019/0282222 A1* | 9/2019 | Shibley | A61B 17/0218 |

FOREIGN PATENT DOCUMENTS

| | | | |
|---|---|---|---|
| DE | 4204210 | A1 | 8/1992 |
| DE | 19624826 | A1 | 1/1998 |
| EP | 0947166 | A2 | 10/1999 |
| EP | 1685802 | A1 | 8/2006 |
| EP | 1707126 | A1 | 10/2006 |
| EP | 2005900 | A2 | 12/2008 |
| EP | 2184014 | A2 | 5/2010 |
| EP | 2436313 | A2 | 4/2012 |
| EP | 2474270 | A2 | 7/2012 |
| FR | 1272412 | A | 9/1961 |
| GB | 246009 | A | 1/1926 |
| WO | 9315675 | A1 | 8/1993 |
| WO | 9509666 | A1 | 4/1995 |
| WO | 0135831 | A1 | 5/2001 |
| WO | 2004002334 | A1 | 1/2004 |
| WO | 2004112571 | A2 | 12/2004 |
| WO | 2005112783 | A1 | 12/2005 |
| WO | 2006110733 | | 10/2006 |
| WO | 2007048078 | A1 | 4/2007 |
| WO | 2007048085 | A2 | 4/2007 |
| WO | 2008114234 | A2 | 9/2008 |
| WO | 2009149146 | A1 | 12/2009 |
| WO | 2011090862 | A2 | 7/2011 |

OTHER PUBLICATIONS

European Search Report EP 11250837.9 dated Sep. 10, 2013.
European Search Report EP 11250838.7 dated Sep. 10, 2013.
European Search Report EP 13170118.7 dated Dec. 5, 2013.
European Search Report EP 12165852 dated Jun. 20, 2012.
http://www.biomaterials.org/week/bio17.cfm, definition and examples of hydrogels.
European Search Report EP 12150271 dated Jan. 14, 2013.
European Search Report EP 12193450 dated Feb. 27, 2013.
European Search Report EP 12189517.1 dated Mar. 6, 2013.
European Search Report EP 12158873 dated Jul. 19, 2012.
European Search Report EP 11250836 dated Sep. 12, 2013.
Extended European Search Report issued in corresponding Appl. No. EP 19153218.3 dated Jun. 21, 2019 (8 pages).

* cited by examiner

SPECIMEN RETRIEVAL DEVICE

CROSS-REFERENCE TO RELATED APPLICATION

This application claims the benefit of and priority to U.S. Provisional Patent Application No. 62/621,189 filed Jan. 24, 2018, the entire disclosure of which is incorporated by reference herein.

TECHNICAL FIELD

The present disclosure relates generally to surgical apparatuses for use in minimally invasive surgical procedures, such as endoscopic and/or laparoscopic procedures, and more particularly, the present disclosure relates to a surgical apparatus including a specimen retrieval bag assembly and a vacuum tube for accessing the bag assembly and collecting body tissue(s) and/or body fluid(s) during these procedures.

BACKGROUND

Minimally invasive surgery, such as endoscopic surgery, reduces the invasiveness of surgical procedures. Endoscopic surgery involves surgery through body walls, for example, viewing and/or operating on the ovaries, uterus, gall bladder, bowels, kidneys, appendix, etc. There are many common endoscopic surgical procedures, including arthroscopy, laparoscopy, gastroentroscopy and laryngobronchoscopy, just to name a few. In these procedures, trocars are utilized for creating incisions through which the endoscopic surgery is performed. Trocar tubes or cannula devices are extended into and left in place in the abdominal wall to provide access for endoscopic surgical tools. A camera or endoscope is inserted through a trocar tube to permit the visual inspection and magnification of the body cavity. The surgeon can then perform diagnostic and/or therapeutic procedures at the surgical site with the aid of specialized instrumentation, such as forceps, graspers, cutters, applicators, and the like, which are designed to fit through additional cannulas. To protect the opening from accidental penetration by the surgical instruments, wound retractors are often placed across the opening.

When removing certain tissues from the body cavity, for example tumor tissue, it is important that the tumor tissue does not come into contact with healthy or uninvolved tissue, so as in this way to avoid metastasis and avoid harming the patient. Minimally invasive surgical procedures, however, may be limited where large size tumors or large masses of tissue have to be removed from a body cavity. If tumor tissue or tissue parts have to be removed, they may be introduced into an "extraction bag," also referred to herein as a "specimen bag," at the site where the tumor or diseased tissue has been detached from the surrounding tissue, after which the specimen bag is withdrawn from the body, normally through a trocar or similar device, thereby minimizing contact of the diseased tissue with healthy tissue.

Improved wound retractors and specimen bags, including those capable of use with a vacuum source, for use in minimally invasive surgical procedures remain desirable.

SUMMARY

The present disclosure is directed to surgical apparatuses and kits for use in minimally invasive surgery. The surgical apparatus includes a wound retractor having a specimen bag attached thereto, for placement of diseased tissue therein. In embodiments, the kit of the present disclosure includes the surgical apparatus and a vacuum tube for assisting in removing tissue specimens from the body.

In some embodiments, a kit of the present disclosure includes a wound retractor and specimen bag assembly including a wound retractor and a specimen bag. The wound retractor includes a proximal ring, a distal ring, and a film disposed between the proximal ring and the distal ring, with the specimen bag attached to the distal ring of the wound retractor. The kit also includes a vacuum tube.

In embodiments, the proximal ring of the wound retractor defines a generally circular opening and is deformable.

In some embodiments, the distal ring of the wound retractor defines a generally circular opening and is deformable.

In embodiments, a length of the film of the wound retractor between the proximal ring and the distal ring is adjustable.

In other embodiments, the specimen bag is attached to the distal ring of the wound retractor by a method such as adhesive bonding, welding, heat-sealing, and combinations thereof.

In some embodiments, the wound retractor includes a tether.

In embodiments, the vacuum tube includes a distal portion defining a generally circular opening, a narrower proximal portion defining a narrower, generally circular opening, and an elongate shaft defining a lumen between the distal portion and the narrower proximal portion.

In some embodiments, the vacuum tube includes a valve.

In other embodiments, the kit of the present disclosure further includes a vacuum source adapted to communicate with the vacuum tube. In some embodiments, the vacuum source includes a syringe.

In yet other embodiments, a kit of the present disclosure includes a wound retractor and specimen bag assembly including a wound retractor and a specimen bag, the wound retractor including a proximal ring, a distal ring, and a film disposed between the proximal ring and the distal ring, the specimen bag being attached to the distal ring of the wound retractor. In embodiments, the kit also includes a vacuum tube, and a vacuum source including a syringe adapted to communicate with the vacuum tube.

In some embodiments, the proximal ring of the wound retractor defines a generally circular opening and is deformable. The distal ring of the wound retractor may also define a generally circular opening and is deformable.

In embodiments, a length of the film of the wound retractor between the proximal ring and the distal ring is adjustable.

In some embodiments, the specimen bag is attached to the distal ring of the wound retractor by a method such as adhesive bonding, welding, heat-sealing, and combinations thereof.

In other embodiments, the wound retractor includes a tether.

In embodiments, the vacuum tube includes a distal portion defining a generally circular opening, a narrower proximal portion defining a narrower, generally circular opening, and an elongate shaft defining a lumen between the distal portion and the narrower proximal portion.

In other embodiments, the vacuum tube includes a valve.

Methods of the present disclosure are also provided. In embodiments, a method of the present disclosure includes inserting a wound retractor and specimen bag assembly including a wound retractor having a proximal ring, a distal ring and a film disposed between the proximal ring and the distal ring, and a specimen bag attached to the distal ring, into a body cavity through a body opening; passing a tissue specimen through an opening defined by the proximal ring, the film and the distal ring of the wound retractor into the specimen bag; removing the proximal ring from the body cavity through the body opening so that the film is adjacent tissue encompassing the body opening; pulling the proximal ring away from the distal ring such that the distal ring is brought into abutment with an inner surface of the tissue surrounding the body opening; rolling the proximal ring about itself such that the film is furled about the proximal ring to bring the proximal ring into abutment with an outer surface of the tissue; introducing a vacuum tube through the proximal ring into the specimen bag; attaching a vacuum source to the vacuum tube; drawing a vacuum through the vacuum tube to draw a portion of the tissue specimen within the specimen bag into the distal portion of the vacuum tube; and removing the vacuum tube possessing the portion of the tissue specimen from the wound retractor.

In embodiments, the method of the present disclosure further includes rolling the proximal ring to retract the incision and bring the proximal ring into abutment with an outer surface of the tissue.

BRIEF DESCRIPTION OF THE DRAWINGS

Various embodiments of the presently disclosed wound retractor and specimen bag assembly are described herein with reference to the drawings wherein.

DETAILED DESCRIPTION

Figure 1:
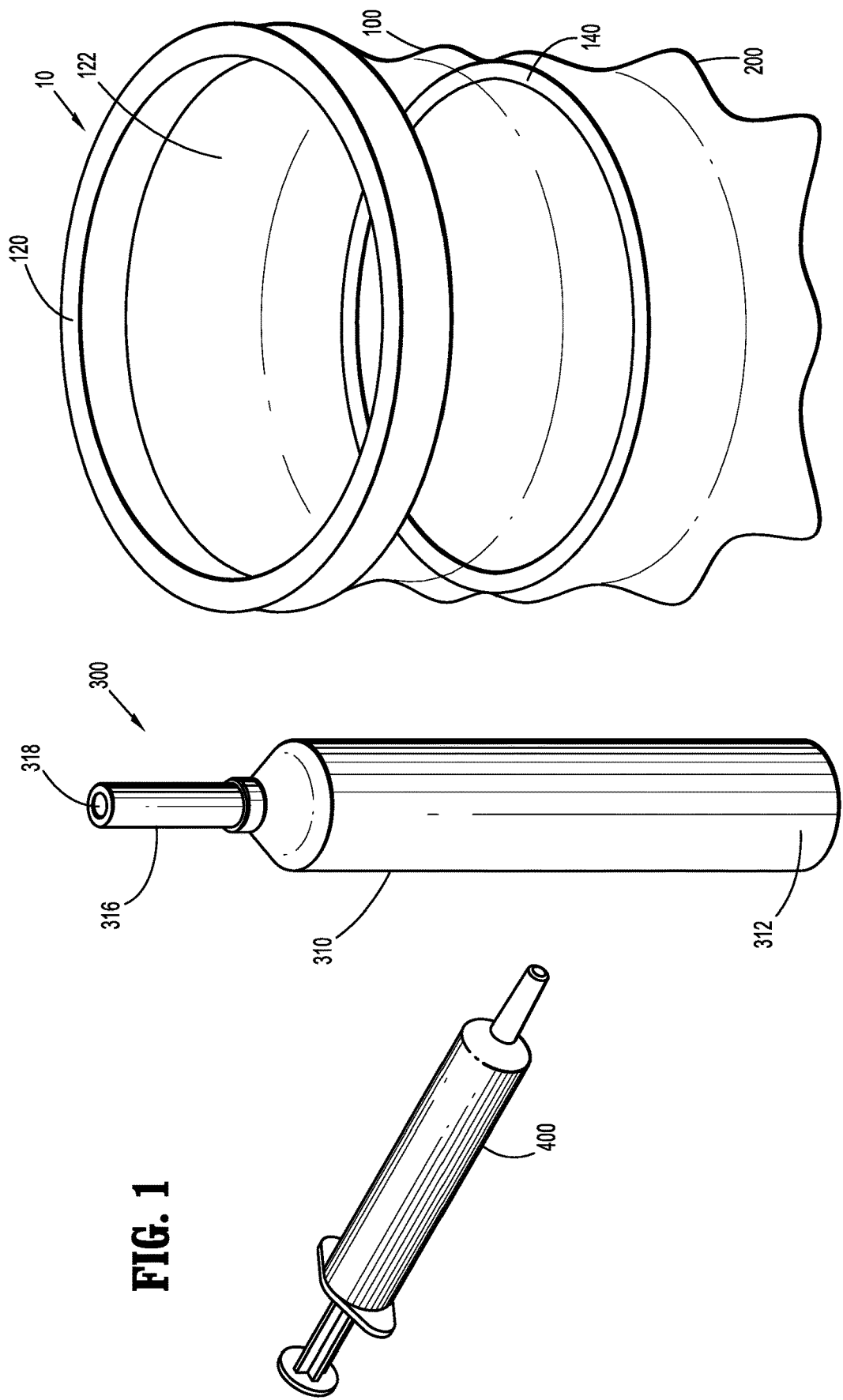
FIG. 1 is a perspective view of components of a kit including an exemplary embodiment of the presently disclosed wound retractor and specimen bag assembly, with a vacuum tube and a vacuum source.
Figure 2:
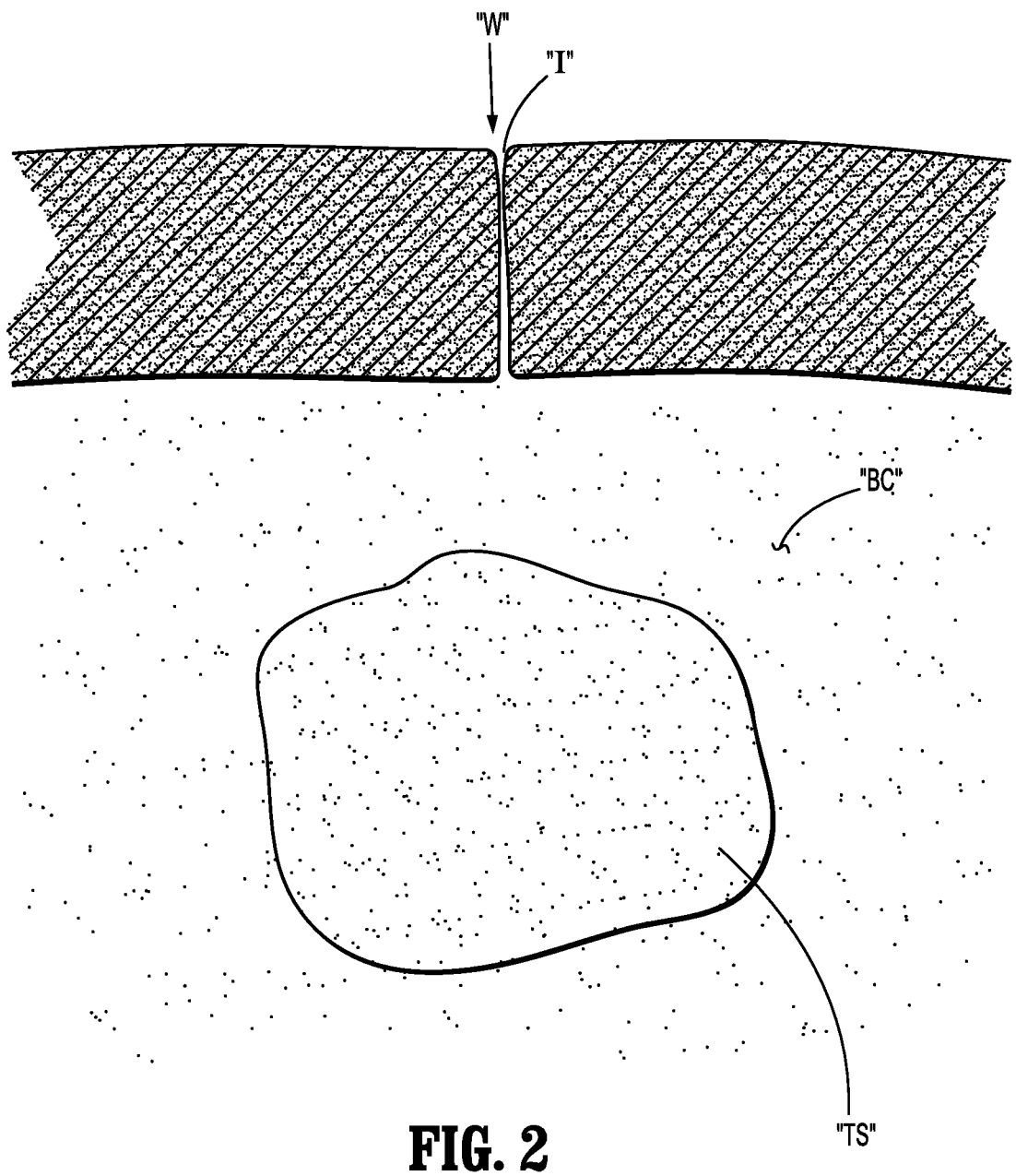
FIG. 2 is a cross-sectional view of a patient's body, showing a wound, incision, and tissue specimen to be removed from the body cavity.
Figure 3:
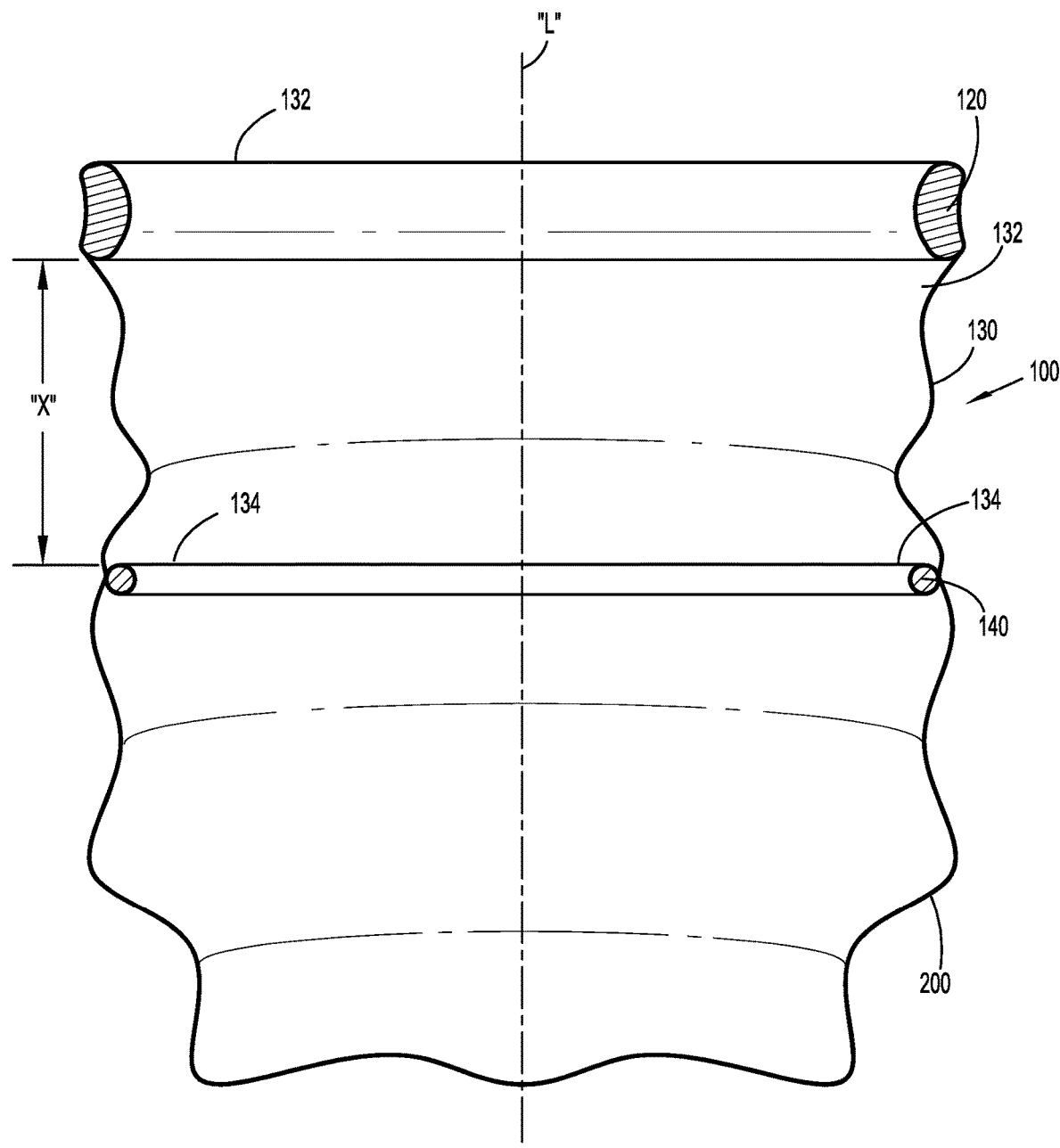
FIG. 3 is a perspective view of the specimen bag and wound retractor assembly shown in FIG. 1.

The present disclosure provides a wound retractor and specimen bag assembly and vacuum tube for use in minimally invasive surgical procedures. As used herein with reference to the present disclosure, minimally invasive surgical procedures encompass laparoscopic procedures and endoscopic procedures, and refer to procedures utilizing scopes or similar devices having relatively narrow operating portions capable of insertion through or a small incision in the skin.

The aspects of the present disclosure may be modified for use with various methods for retrieving tissue specimens during minimally invasive surgical procedures, sometimes referred to herein as minimally invasive procedures. Examples of minimally invasive procedures include, for example, cholecystectomies, appendectomies, nephrectomies, colectomies, splenectomies, and the like.

As used herein, the term distal refers to that portion of a wound retractor and specimen bag assembly which is farthest from the user, while the term proximal refers to that portion of the wound retractor and specimen bag assembly of the present disclosure which is closest to the user.

The wound retractor and specimen bag assembly of the present disclosure includes a wound retractor with a specimen bag affixed thereto. The wound retractor component includes a sleeve member possessing at least two rings, including a proximal ring and a distal ring, with a film extending between the two rings. The specimen bag component is attached to the distal ring of the wound retractor. In use, the specimen bag assembly is passed through an incision and placed within a body cavity, and tissue to be removed therefrom, referred to in embodiments as a "tissue specimen", is passed through the wound retractor component and placed within the specimen bag. The proximal ring of the wound retractor component is then removed from the body cavity and placed adjacent the skin on an outside surface of the body adjacent the incision, with the distal ring of the sleeve member and the specimen bag remaining within the body, so that the film extends through the incision and is adjacent the tissue encompassing the incision. The presently disclosed wound retractor and specimen bag assembly is suitable for use in any procedure where access to the interior of the body is limited to one or more relatively small incisions, as in minimally invasive procedures.

Kits of the present disclosure include both the wound retractor and specimen bag assembly described above, as well as a vacuum tube assembly. The vacuum tube assembly permits removal of tissue specimens from the specimen bag without the need for breaking up the tissue, sometimes referred to herein as morcellation of tissue, with a scalpel or some other morcellation device.

Embodiments of the present disclosure will now be described in detail with reference to the drawings, in which like reference numerals designate identical or corresponding elements in each of the several views. In the following description, well-known functions or constructions are not described in detail to avoid obscuring the present disclosure in unnecessary detail.

FIG. 1 illustrates a kit of the present disclosure including a wound retractor and specimen bag assembly 10 in accordance with the present disclosure. The wound retractor and specimen bag assembly 10 encompasses both a wound retractor 100 and a specimen bag 200. The kit of the present disclosure also includes a vacuum tube 300 and a vacuum source, in embodiments a syringe 400, for drawing a vacuum through the vacuum tube 300.

Referring also to FIGS. 2-4B, the wound retractor and specimen bag assembly 10, including the wound retractor 100 and the specimen bag 200, is adapted for insertion into wound "W" through an incision "I" and placement within a body cavity "BC" (FIG. 4A) as described in further detail below. The incision "I" may be a single incision, e.g., through the abdominal or peritoneal lining, or a naturally occurring orifice (i.e. mouth, anus, or vagina).

The wound retractor 100 includes a proximal ring 120, a distal ring 140, and a generally cylindrical film 130 disposed therebetween. The wound retractor and specimen bag assembly 10 further defines a longitudinal axis "L" shared by the proximal ring 120, the distal ring 140, and the film 130, as well as the specimen bag 200. It is envisioned that the proximal ring 120 and the distal ring 140 may each be detachably coupled or permanently attached to a proximal end portion 132 and a distal end portion 134, respectively, of the film 130 by any means within the purview of those skilled in the art, e.g., glue, suture, impulse welding, chemical or mechanical bonding, an over molding process, etc. In some embodiments, the proximal ring 120, film 130, and distal ring 140 are monolithically integrated such that the wound retractor 100 is a unitary structure. Attachment of the film 130 to the rings 120, 140 can be continuous around the rings 120, 140 or may be discontinuous, provided the rings 120, 140 are sufficiently secured to the film 130 to allow the film 130 to be rolled about the proximal ring 120 as described below.

The proximal ring 120 and the distal ring 140 are axially aligned along longitudinal axis "L" with the film 130 disposed therebetween, as noted above. The proximal ring 120 has a generally circular configuration that defines a circular opening 122 (see FIG. 1) and is rollable about the proximal ring 122 to tension the film 130 and retract the incision "I". More specifically, the proximal ring 120 can be rolled towards or away from the distal ring 140 along the longitudinal axis "L" to furl or unfurl the film 130 about the proximal ring 120. The distal ring 140 also has a generally circular configuration that defines a generally circular opening (not shown).

It is envisioned that the proximal ring 120 and the distal ring 140 may be fabricated from resilient materials such that the proximal ring 120 and the distal ring 140 may temporarily deform into a generally oblong configuration during insertion of the wound retractor 100 through an incision "I" while reverting to a generally circular configuration during use. For example, thermoplastic polyurethanes sold under the name PELLETHANE®, offers flexibility and a wide range of hardnesses. The proximal ring 120, for example, may be fabricated from PELLETHANE® 2363-80A, PELLETHANE® 2363-90A, a 50/50 composition of PELLETHANE® 2363-80A and PELLETHANE® 2363-90A, or any alternatives known in the art. The distal ring 140 may be fabricated from, for example, PELLETHANE® 2363-90A for the extra small and small size, PELLETHANE® 2363-55D for the medium and large size, a 50/50 composition of PELLETHANE® 2363-90A and PELLETHANE® 2363-55D for the large size, or any alternatives within the purview of those skilled in the art. The proximal ring 120 and the distal ring 140 may be fabricated from the same or different materials.

The film 130 defines a generally cylindrical shape to form a lumen between the proximal ring 120 and the distal ring 140. The circular configuration of the proximal and distal rings 120 and 140, respectively, maintains the film 130 in an expanded state to maintain the lumen in a non-collapsed state. The film 130 is coupled to the proximal ring 120 at the proximal end portion 132 and is coupled to the distal ring 140 at the distal end portion 134, such that the film 130 does not slide or move relative to a surface of either the proximal ring 120 or the distal ring 140. The film 130 may be fabricated from a clear, non-elastomeric material, e.g., a polyurethane. Alternately, it is envisioned that the film 130 may be formed from a variety of materials including opaque and clear materials.

The length "X" (FIG. 3) between the proximal ring 120 and the distal ring 140 is adjustable. More specifically, the length "X" can be decreased by rolling the proximal ring 120 towards the distal ring 140 to furl the film 130 about the proximal ring 120. Similarly, the length "X" can be increased by rolling the proximal ring 120 away from the distal ring 140 to unfurl the film 130 from about the proximal ring 120. As discussed above, as the proximal ring 120 is rolled towards or away from the distal ring 140, the film 130 furls or unfurls about the proximal ring 120. It should be appreciated that as the film 130 is furled about the proximal ring 120, it reduces the length "X" of the film 130, so the tension in the film between the proximal ring 120 and distal ring 140 is increased to provide a radially outward force within the incision "I".

It is envisioned that the wound retractor 100 may come in a variety of sizes to appropriately fit and accommodate a range of incision diameters. For example, for an extra small wound retractor, the outer diameter of the proximal ring 120 and the distal ring 140 may be about 2.5 inches; for a small wound retractor, the outer diameter of the proximal ring 120 and the distal ring 140 may be about 3.9 inches; for a medium sized wound retractor, the outer diameter of the proximal ring 120 and the distal ring 140 may be about 5.1 inches; for a large wound retractor, the outer diameter of the proximal ring 120 and the distal ring 140 may be about 7.5 inches; and for an extra-large wound retractor, the outer diameter of the proximal ring 120 and the distal ring 140 may be about 9.4 inches.

Specimen bags of the present disclosure are made of flexible and durable materials within the purview of those skilled in the art, in embodiments, polymeric materials. The specimen bags are inflatable and capable of allowing a surgeon to introduce cutting devices into the specimen bag to reduce the size of the tissue specimen therein, thereby facilitating removal of the specimen bag from the body. Materials used to form the specimen bags are antistatic, pyrogen-free, non-toxic and sterilizable. In embodiments, materials used to form the film portion of the wound retractor described above may be used to form the specimen bag. In other embodiments, the specimen bag is formed of materials that are different from those used to form the film of the wound retractor. The specimen bag may be opaque or clear.

The specimen bag 200 may be joined to the distal ring 140 of the wound retractor at the distal portion 134 of the film 130 by methods within the purview of those skilled in the art, including, but not limited to, adhesive bonding, welding, heat-sealing, combinations thereof, and the like. Alternatively, the specimen bag 200 can be integrally formed with the film 130, in embodiments of the same material.

As discussed above, both the proximal ring 120 and the distal ring 140 may be collapsed from the generally circular configuration to a generally oblong configuration (not shown) for insertion, along with the specimen bag 200, through incision "I". More specifically, as the practitioner squeezes opposing sides of the proximal ring 120 and the distal ring 140 radially inwards, the generally circular openings of the proximal ring 120 and the distal ring 140 are deformed from the generally circular configuration to a generally oblong configuration (not shown) such that the proximal ring 120 and the distal ring 140 assume a smaller profile for ease of insertion through incision "I". Once inserted, the practitioner releases the proximal ring 120 and distal ring 140 and the resiliency of the material urges the proximal ring 120 and the distal ring 140 towards their generally circular configurations.

In embodiments, where there is concern that the tissue specimen "TS" within the specimen bag 200 is diseased, for example cancerous, and it is desired to minimize contact of the tissue specimen "TS" with healthy tissue, but morcellation or other means for breaking up the tissue within the specimen bag 200 are not feasible or desired (for fear of damaging the specimen bag 200 and/or the wound retractor 100), a vacuum tube 300 may be inserted through the lumen of the wound retractor 100 into the specimen bag 200 to remove tissue specimen "TS" from the body cavity "BC".

Figures 6, 7:
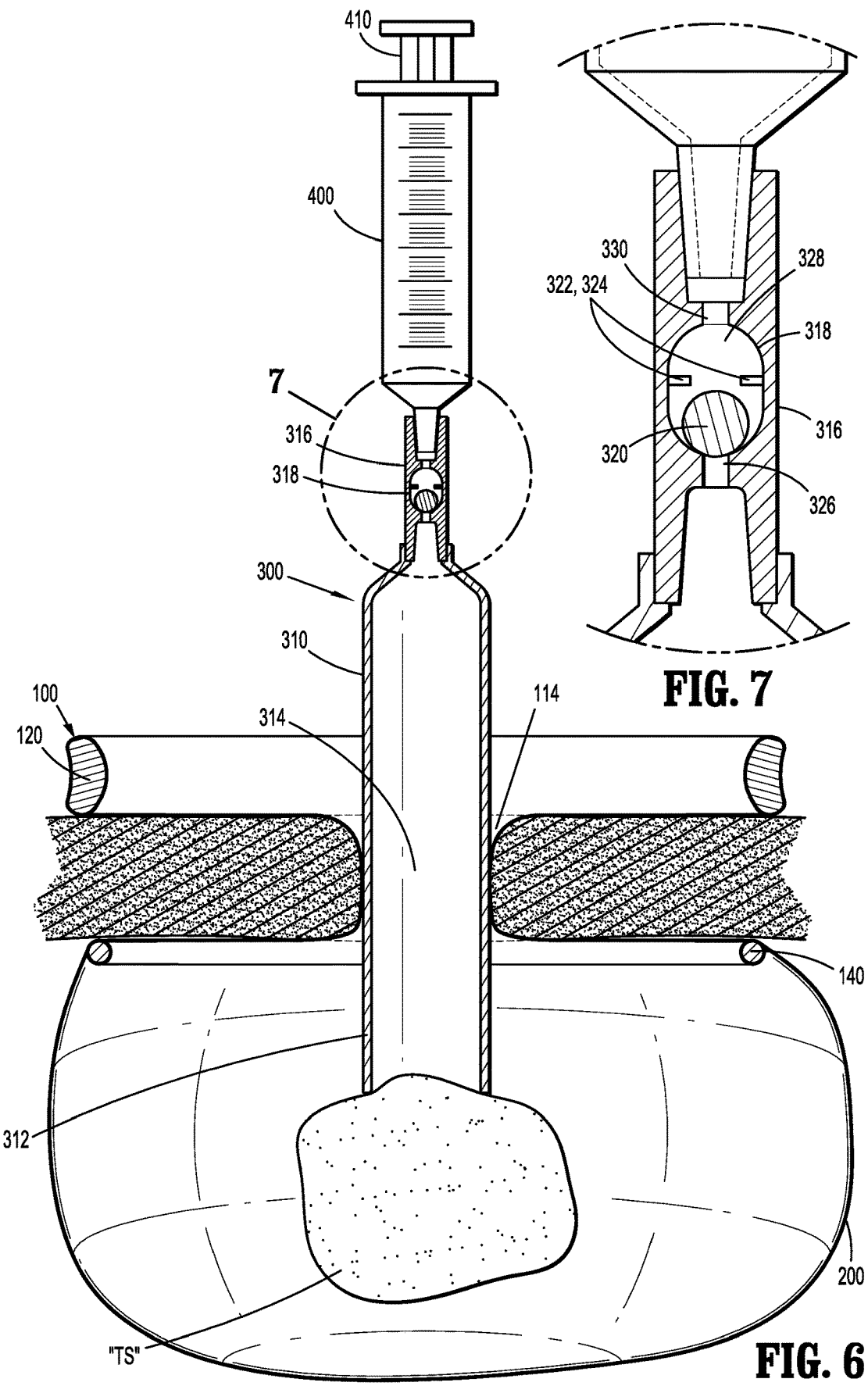
FIG. 6 is a partial cross-sectional view of the wound retractor and specimen bag assembly shown in FIG. 5, with a vacuum tube inserted through the wound retractor into the specimen bag and a vacuum source affixed to the vacuum tube.
FIG. 7 is an enlarged view of the indicated area of detail shown in FIG. 6.
Figures 8, 9:
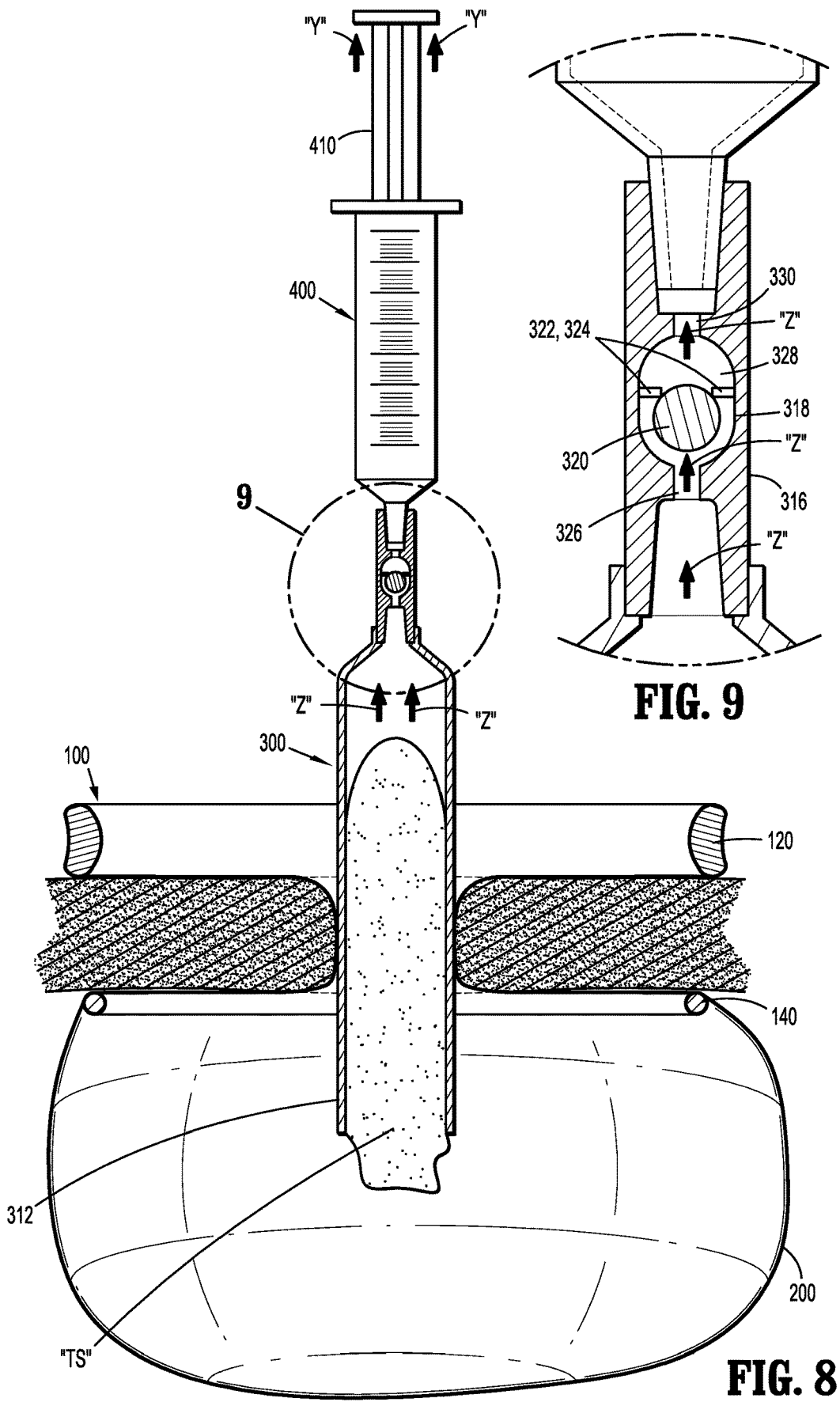
FIG. 8 is a partial cross-sectional view of the wound retractor and specimen bag assembly shown in FIG. 6, showing the vacuum source drawing a vacuum through the vacuum tube and pulling tissue from the specimen bag into the vacuum tube.
FIG. 9 is an enlarged view of the indicated area of detail shown in FIG. 8.

The kit (FIG. 1) of the present disclosure includes a vacuum tube 300. The vacuum tube 300 has an elongate body 310 defining a lumen 314 (FIG. 6). The elongate body 310 has a distal portion 312 defining a generally circular opening and, compared with the distal portion 312, a narrower proximal portion 316. The narrower proximal portion 316, compared with the distal portion 312, defines a narrower lumen with a narrower, generally circular opening 318.

The vacuum tube 300 may be formed of hard, rigid materials. Suitable materials for forming the vacuum tube include, for example, polyolefins such as polyethylene (including ultra high molecular weight polyethylene) and polypropylene including atactic, isotactic, syndiotactic, and blends thereof; polyethylene glycols (PEGs); polyethylene oxides; copolymers of polyethylene and polypropylene; polyisobutylene and ethylene-alpha olefin copolymers; fluorinated polyolefins such as fluoroethylenes, fluoropropylenes, fluoroPEGs, and polytetrafluoroethylene; polyamides; polyamines; polyimines; polyesters such as polyethylene terephthalate, polyethylene naphthalate, polytrimethylene terephthalate, and polybutylene terephthalate; polyethers; polybutester; polytetramethylene ether glycol; 1,4-butanediol; polyurethanes; acrylic polymers; methacrylics; vinyl halide polymers and copolymers such as polyvinyl chloride; polyvinyl alcohols; polyvinyl ethers such as polyvinyl methyl ether; polyvinylidene halides such as polyvinylidene fluoride and polyvinylidene chloride; polychlorofluoroethylene; polyacrylonitrile; polyaryletherketones; polyvinyl ketones; polyvinyl aromatics such as polystyrene; polyvinyl esters such as polyvinyl acetate; copolymers of vinyl monomers with each other and olefins such as ethylene-methyl methacrylate copolymers; acrylonitrile-styrene copolymers; acrylonitrile butadiene styrene resins; ethylene-vinyl acetate copolymers; alkyd resins; polycarbonates; polyoxymethylenes; polyphosphazines; polyimides; epoxy resins; aramids; silicones; and copolymers and combinations thereof.

The kit of the present disclosure also includes a vacuum source, in embodiments a syringe 400, for drawing a vacuum through the vacuum tube 300, thereby removing the tissue specimen "TS" from the specimen bag 200 by drawing the tissue specimen "TS" into the distal portion 312 of the vacuum tube 300. Other possible sources for drawing a vacuum include, for example, a mechanically or manually operated pump (not shown), a simple electric vacuum pump (not shown), or other similar means. The narrower proximal portion 316 of the vacuum tube 300 is couplable to the vacuum source, in embodiments the syringe 400. Means for coupling the narrower proximal portion 316 of the vacuum tube 300 to the vacuum source, in embodiments the syringe 400, are within the purview of those skilled in the art and include, for example, friction fitting, the use of seals within the lumen of circular opening 318 of the narrower proximal portion 316 of the vacuum tube 300, a luer-type coupling, combinations thereof, and the like.

With reference to FIGS. 2 and 4-11, a method of operating the surgical apparatus 10 in accordance with the present disclosure will be described. As depicted in FIGS. 2 and 4A-5, in order to access a tissue specimen "TS" positioned within a body cavity "BC" (FIG. 2), the surgeon first collapses and deforms the proximal ring 120 and the distal ring 140 of the wound retractor 100 into an oblong configuration for insertion into wound "W" through incision "I" (FIG. 4A). Once the wound retractor 100 and the specimen bag 200 are placed through incision "I" and the proximal ring 120 and the distal ring 140 are released, the proximal ring 120 and distal ring 140 resume their generally circular configuration so that the surgical apparatus 10 is adjacent the tissue specimen "TS" to be removed from the body cavity (FIG. 4A). The surgeon can then introduce tissue specimen "TS" through the proximal ring 120, the film 130, and the distal ring 140 into the specimen bag 200 by use of a forceps, grasper, or any other suitable medical device.

Figure 4A:
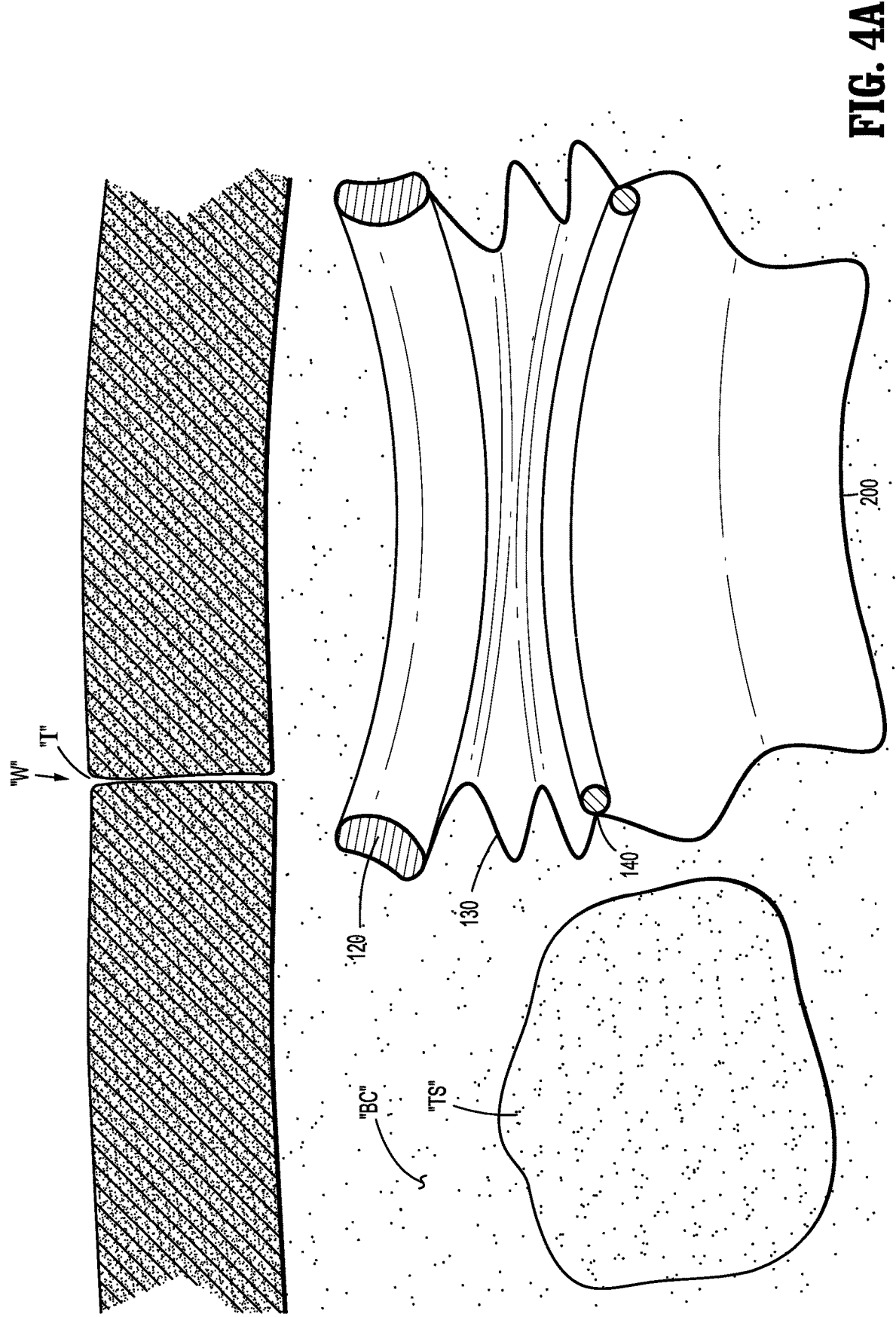
FIG. 4A is a cross-sectional view of the wound retractor and specimen bag assembly shown in FIG. 3 in a body cavity, adjacent tissue to be removed from the body cavity.
Figure 4B:
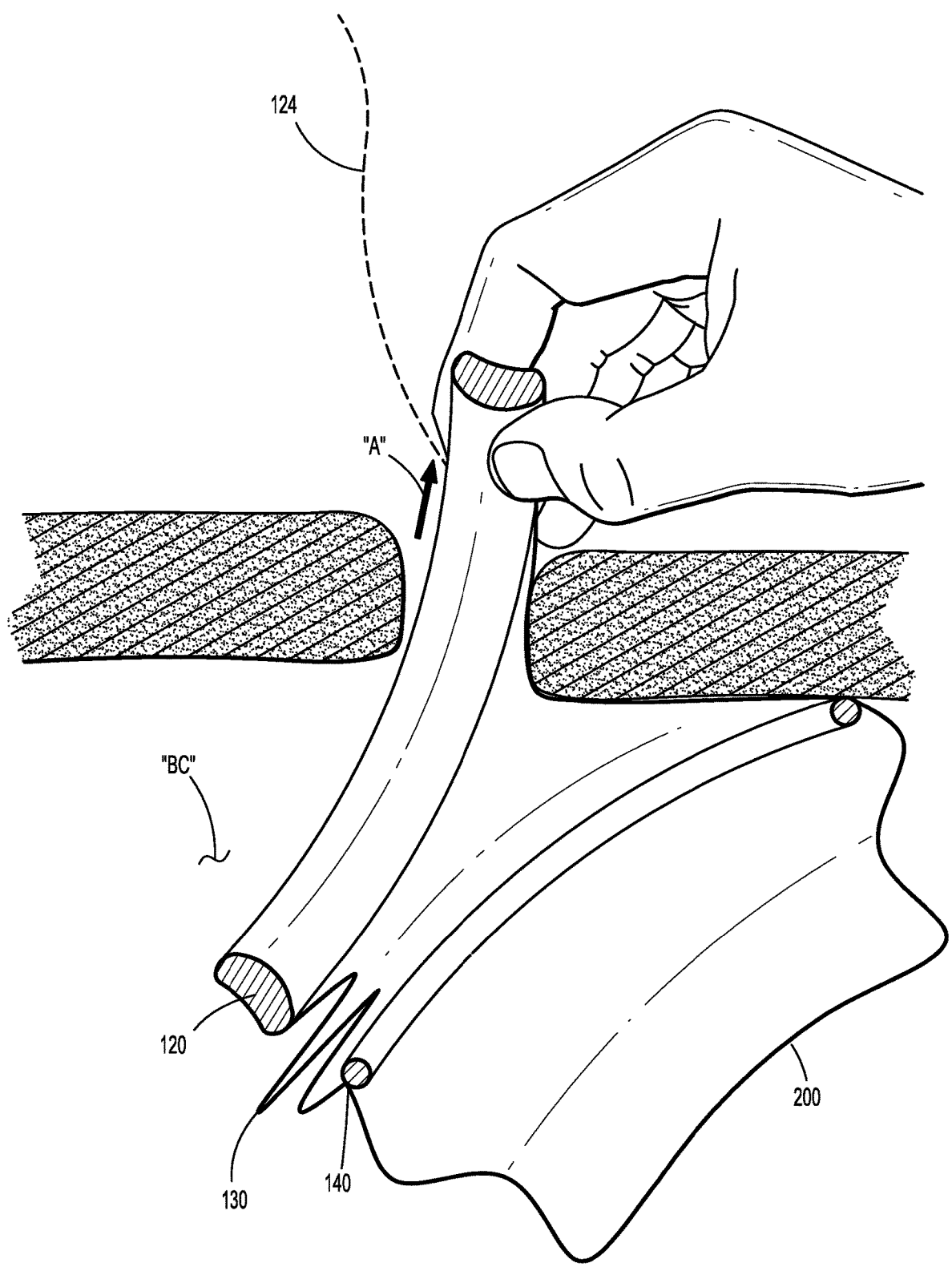
FIG. 4B is a perspective, partial cross-sectional view during removal of the wound retractor and specimen bag assembly shown in FIG. 4A from a body cavity through the incision.

Once tissue specimen "TS" has been introduced into the specimen bag 200, the surgeon then collapses and deforms the proximal ring 120 using a forceps, grasper, or similar instrument and withdraws the proximal ring 120 through the incision "I". In other embodiments, the proximal ring 120 has a tether 124 thereon (shown in phantom in FIG. 4B), which may be pulled proximally by the surgeon to withdraw the proximal ring 120 from the body cavity "BC". As depicted in FIG. 4B, the surgeon may pull the proximal ring 120 (indicated by arrows "A" in FIG. 4B) to remove the proximal ring 120 from the incision "I" after the specimen "TS" is positioned within the specimen bag 200.

Figure 5:
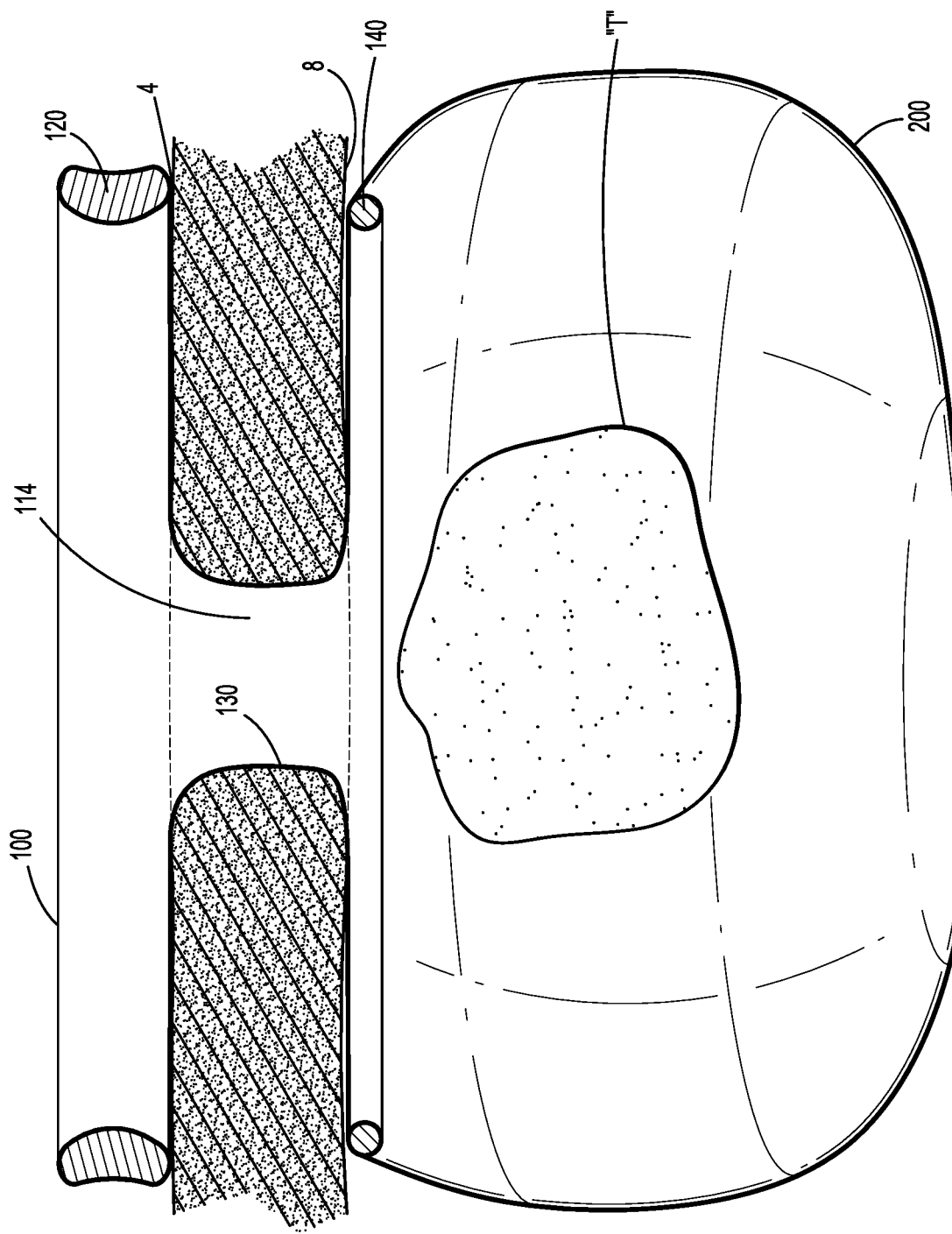
FIG. 5 is a perspective view of the wound retractor and specimen bag assembly shown in FIG. 4B with the wound retractor inserted into the incision in tissue and the specimen bag positioned within the body cavity.

As shown in FIG. 5, the proximal ring 120 is removed from the body cavity through incision "I" so that it rests on the outer skin 4 adjacent incision "I" and the surgeon adjusts the film 130 and the proximal ring 120, e.g., pulling the proximal ring 120 proximally to tension the film 130, such that the distal ring 140 comes into abutment with an inner surface 8 of wound "W". The distal ring 140 is positioned adjacent the inner surface 8 of wound "W", and reverts to its generally circular configuration so that the generally circular opening of distal ring 140 encompasses the inner surface 8 of the wound "W" (FIG. 5).

With the distal ring 140 in abutment with the inner surface 8 of wound "W", the proximal ring 120 is rolled distally towards the distal ring 140 and the outer surface 4 of wound "W" to a desired position, such that the film 130 is furled about the proximal ring 120 (not shown) and thereby tensioned.

Referring to FIG. 5, once the wound retractor 100 and the specimen bag 200 are in position, surgical tools and instruments may pass through a lumen 114 of the wound retractor 100 with the distal ring 140 in abutment to the inner surface 8 of wound "W", and the proximal ring 120 rolled to a desired position and/or brought into abutment to the outer surface 4 of wound "W". The wound retractor 100 may be tensioned further to provide retraction of incision "I", increasing the incision diameter.

Figure 10:
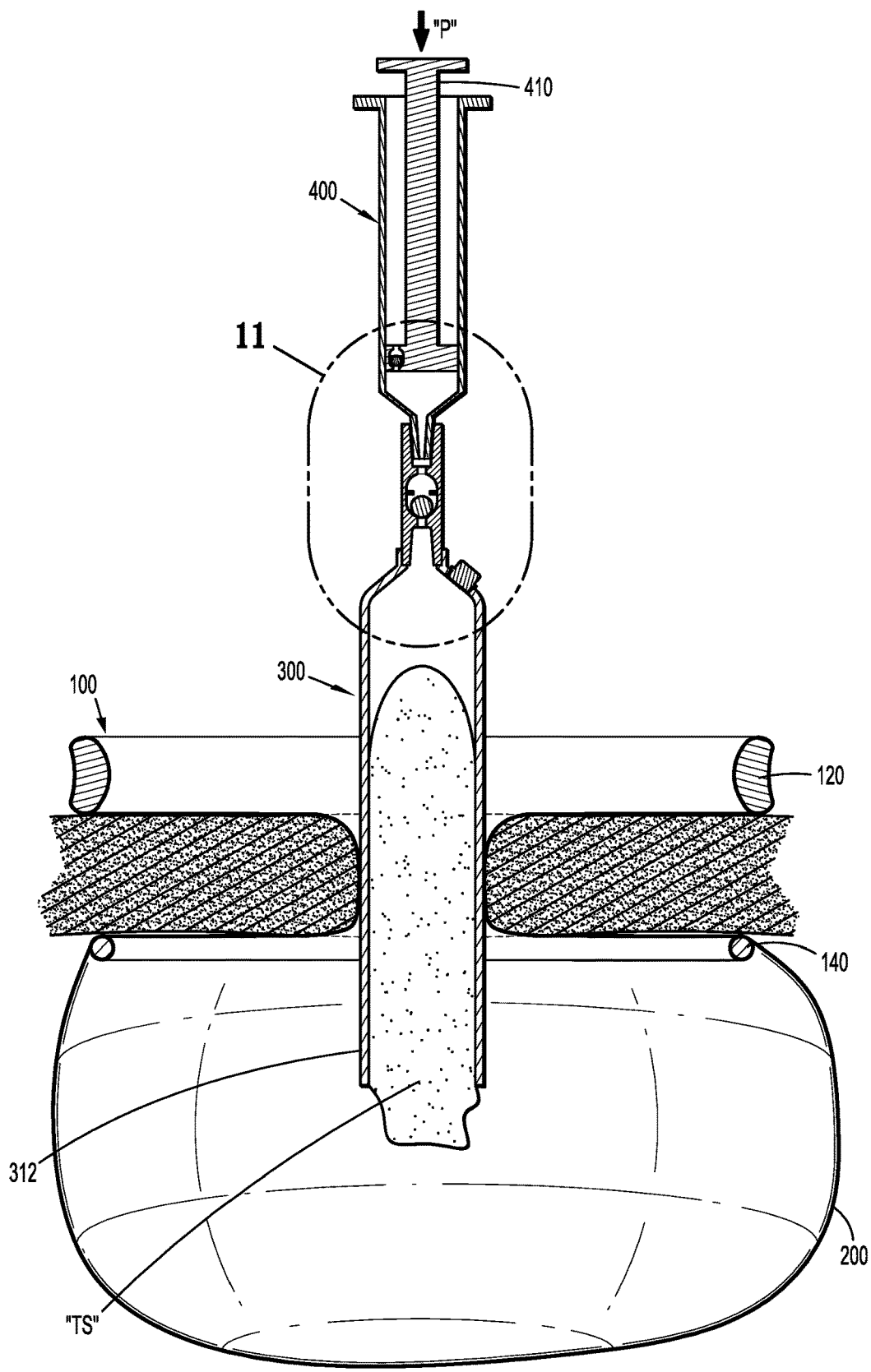
FIG. 10 is an alternate partial cross-sectional view of the wound retractor and specimen bag assembly shown in FIG. 6, showing the vacuum source drawing a vacuum through the vacuum tube and pulling tissue from the specimen bag into the vacuum tube.
Figure 11:
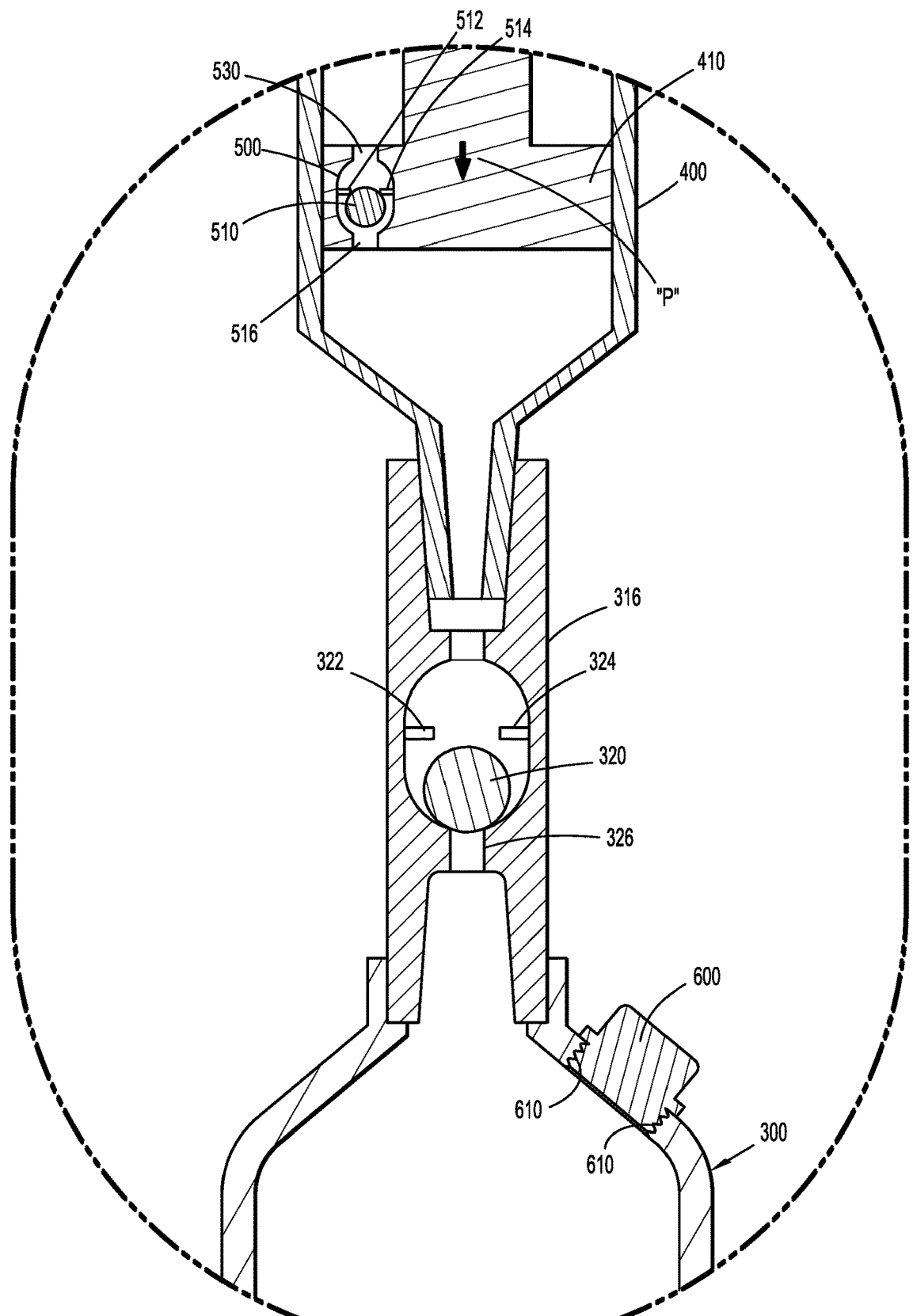
FIG. 11 is an enlarged view of the indicated area of detail shown in FIG. 10.

Referring briefly to FIG. 6, where the tissue specimen "TS" in the specimen bag is too large to be removed through the incision, a vacuum tube 300 is introduced through the lumen 114 of wound retractor 100 (FIG. 6). As depicted in FIGS. 6-11, a syringe 400, or any other device capable of drawing a vacuum, may then be attached to the narrower proximal portion 316 of the vacuum tube 300 to draw a vacuum within the lumen 314 of the vacuum tube 300, thereby drawing the tissue specimen "TS" contained within the specimen bag 200 into the distal end portion 312 of the vacuum tube 300.

Where the syringe 400 is used as the vacuum source, the plunger 410 of the syringe 400 may first be pushed distally (indicated by arrows "P" in FIGS. 10 and 11) to evacuate air from the syringe 400. As depicted in FIGS. 10 and 11, the plunger 410 may possess a small one-way valve to permit the evacuation of air from the syringe 400. The one-way valve can be any type of trap allowing the one way flow of air, out of the syringe 400. As shown in FIGS. 10 and 11, an example of a suitable one-way valve includes a ball valve 500. The air present in the syringe 400 evacuates itself thru the ball valve 500 when the plunger 410 is pushed distally (indicated by arrows "P" in FIGS. 10 and 11). No air goes back down into the syringe 400.

As shown in FIG. 11, the ball valve 500 possesses spokes 512, 514 which prevent the ball 500 from blocking a proximal opening 530 of the ball valve 500, while at the same time permitting air to pass from the syringe 400, through a distal opening 516 of the ball valve 500, through the proximal opening 530 of the ball valve 500, and out of the syringe 400.

As depicted in FIGS. 6-9, the vacuum tube 300 includes a valve within the narrower proximal portion 316 of the vacuum tube 300. In embodiments, as depicted in FIGS. 6-9, the valve may include a ball valve 318, including a ball 320, and projections 322, 324 projecting into a lumen 328 of the ball valve 318. The projections 322, 324 prevent the ball 320 from blocking a proximal opening 330 of the ball valve 318, while at the same time permitting air (indicated by arrows "Z" in FIG. 9) to pass from the specimen bag 200, through a distal opening 326 of the ball valve 318, through the lumen 328 of the ball valve 318, through the proximal opening 330 of the ball valve 318, and out of the narrower proximal portion 316 of the vacuum tube 300. Other valves, such as one-way valves, check valves, or any other valve arrangement, may be included within the narrower proximal portion 316 of the vacuum tube 300 to assist in drawing and maintaining a vacuum within the lumen 314 of the vacuum tube 300.

In use, the plunger 410 of the syringe 400 is pushed distally (indicated by arrows "P" in FIGS. 10 and 11) so that the air within the syringe 400 evacuates itself thru the ball valve 500. The plunger 410 of the syringe 400 is then pulled proximally (indicated by arrows "Y" in FIG. 8) to create a vacuum capable of drawing tissue specimen "TS" from the specimen bag 200 into the distal end portion 312 of the vacuum tube 300. Where necessary, the above cycle (pushing the plunger 410 of the syringe 400 distally and then pulling the plunger 410 of the syringe 400 proximally) may be repeated to ensure an adequate vacuum state is created, capable of drawing tissue specimen "TS" from the specimen bag 200 into the distal end portion 312 of the vacuum tube 300. The process may be repeated multiple times in order to achieve the vacuum necessary to draw the tissue specimen "TS" into the vacuum tube 300.

For example, the plunger 410 of the syringe 400 is pushed down at least a second time to repeat the cycle (indicated by arrows "P" in FIGS. 10 and 11), in preparation for another proximal pull (indicated by arrows "Y" in FIG. 8) to evacuate more air (indicated by arrows "Z" in FIG. 9) from the vacuum tube 300. The ball valve 500 of the plunger 410 of the syringe 400 allows for repetition of the cycle to create an adequate vacuum without the need to disconnect the syringe 400 after each proximal pull.

Once the tissue specimen "TS" is pulled into the distal end portion 312 of the vacuum tube 300, the vacuum tube 300 may be removed from the wound retractor 100. In embodiments, if the tissue specimen "TS" to be removed separates and portions thereof remain in the specimen bag 200 as tissue specimen "TS" is pulled into the distal end portion 312 of the vacuum tube 300, the surgeon may grab those additional pieces of tissue with a forceps or other grasper, and/or use a vacuum source for removal of any remaining portion of the tissue specimen "TS" from the specimen bag 200. In other embodiments, the volume of the tissue specimen "TS" in the specimen bag 200, as well as any fluids from the tissue specimen "TS", may be reduced to a point that specimen bag 200, with any remaining tissue and/or fluids therein, may pass through incision "I" without need for any further vacuum.

In embodiments, once the vacuum tube 300 is removed from the wound retractor 100, a pin (not shown) or some similar means may be used to lift the ball 320 so that it no longer blocks the distal opening 326 of the narrower proximal portion 316 of the vacuum tube 300, to let air into the vacuum tube 300, and assist in releasing the tissue specimen "TS" from the vacuum tube 300. Alternatively, as depicted in FIGS. 10 and 11, in embodiments, the vacuum tube 300 may have a plug 600. As depicted in FIG. 11, in embodiments the vacuum tube 300 may have a threaded opening 610 and the plug 600 may be threaded and rotatably received within the threaded opening 610. Rotation of the plug 600 allows for its attachment and/or removal from the vacuum tube 300. Removal of the plug 600 from the threaded opening 610 lets air into the vacuum tube 300, and assists in releasing the tissue specimen "TS" from the vacuum tube 300.

Once the vacuum tube 300 has been removed from the wound retractor 100, the surgeon then collapses and deforms the distal ring 140 of the wound retractor 100 using a forceps, grasper, or similar instrument and the distal ring 140 and specimen bag 200 are withdrawn through the incision "I". In other embodiments, the distal ring 140 has a tether thereon (not shown), which may be pulled proximally by the surgeon to remove the distal ring 140 and the specimen bag 200 from the body cavity "BC".

After the specimen bag 200 is removed from the body cavity "BC", any tissue remaining therein can be removed from the specimen bag 200 for further examination or the specimen bag 200 can be discarded.

The kits and specimen bags of the present disclosure provide safe tissue extraction at the end of minimally invasive surgical procedures. Diseased tissue may be removed from the body without seeding of spilled tissue cells inside the abdomen. The design of the wound retractor/specimen bags of the present disclosure, with the vacuum tube described above, allows for the surgeon to remove tissue from the body without the need for morcellators or other mechanical devices that otherwise could tear the specimen bag and possibly release tissue contents back into the body of the patient. It is further envisioned that the methods of using the specimen bags of the present disclosure may be modified to accommodate needs of a given procedure and/or the preferences of the surgeon. It is further envisioned that the embodiments disclosed herein may be used to remove any tissue or object from the body.

It will be understood that various modifications may be made to the embodiments disclosed herein. For example, other methods for introducing specimen bags of the present disclosure into the body of a patient may be used. Additionally, other specimen bag shapes may be used. Further, the terminology of similar components with the various embodiments should not be construed as specific to any particular embodiment. Thus, the above description should not be construed as limiting, but merely as exemplifications of preferred embodiments. Those skilled in the art will envision other modifications within the scope and spirit of the claims appended hereto.

What is claimed is:

1. A kit comprising:
    a wound retractor and specimen bag assembly including a wound retractor and a specimen bag, the wound retractor including:
        a proximal ring;
        a distal ring;
        a film disposed between the proximal ring and the distal ring,
        the specimen bag attached to the distal ring of the wound retractor;
    a vacuum tube for removing a tissue specimen from the specimen bag, the vacuum tube including a valve; and
    a vacuum source including a syringe adapted to communicate with the vacuum tube.

2. The kit of claim 1, wherein the proximal ring of the wound retractor defines a circular opening and is deformable.

3. The kit of claim 1, wherein the distal ring of the wound retractor defines a circular opening and is deformable.

4. The kit of claim 1, wherein a length of the film of the wound retractor between the proximal ring and the distal ring is adjustable.

5. The kit of claim 1, wherein the specimen bag is attached to the distal ring of the wound retractor by a method selected from the group consisting of adhesive bonding, welding, heat-sealing, and combinations thereof.

6. The kit of claim 1, wherein the wound retractor includes a tether.

7. The kit of claim 1, wherein the vacuum tube includes a distal portion defining a generally circular opening, a narrower proximal portion defining a narrower, generally circular opening, and an elongate shaft defining a lumen between the distal portion and the narrower proximal portion.

8. A kit comprising:
    a wound retractor and specimen bag assembly including a wound retractor and the specimen bag, the wound retractor including a proximal ring, a distal ring, and a film disposed between the proximal ring and the distal ring, the specimen bag being attached to the distal ring of the wound retractor;
    a vacuum tube for removing a tissue specimen from the specimen bag; and
    a vacuum source including a syringe adapted to communicate with the vacuum tube.

9. The kit of claim 8, wherein the proximal ring of the wound retractor defines a circular opening and is deformable.

10. The kit of claim 8, wherein the distal ring of the wound retractor defines a circular opening and is deformable.

11. The kit of claim 8, wherein a length of the film of the wound retractor between the proximal ring and the distal ring is adjustable.

12. The kit of claim 8, wherein the specimen bag is attached to the distal ring of the wound retractor by a method selected from the group consisting of adhesive bonding, welding, heat-sealing, and combinations thereof.

13. The kit of claim 8, wherein the wound retractor includes a tether.

14. The kit of claim 8, wherein the vacuum tube includes a distal portion defining a generally circular opening, a narrower proximal portion defining a narrower, generally circular opening, and an elongate shaft defining a lumen between the distal portion and the narrower proximal portion.

15. The kit of claim 14, wherein the vacuum tube includes a valve.

16. A kit comprising:
    a wound retractor and specimen bag assembly including a wound retractor and a specimen bag, the wound retractor including:
        a proximal ring,
        a distal ring, and
        a film disposed between the proximal ring and the distal ring,
        the specimen bag attached to the distal ring of the wound retractor;
    a vacuum tube for removing a tissue specimen from the specimen bag, the vacuum tube including a distal portion defining a circular opening, a narrower proximal portion defining a narrower, circular opening, and an elongate shaft defining a lumen between the distal portion and the narrower proximal portion; and
    a vacuum source including a syringe adapted to communicate with the vacuum tube.

17. The kit of claim 16, wherein the proximal ring of the wound retractor defines a circular opening and is deformable, the distal ring of the wound retractor defines a circular opening and is deformable, and a length of the film of the wound retractor between the proximal ring and the distal ring is adjustable.

* * * * *